United States Patent [19] [11] 3,956,364
Singer [45] May 11, 1976

[54] NEMATOCIDAL N-CYANOFORMYL CARBAMATES

[75] Inventor: Malcolm S. Singer, Richmond, Calif.

[73] Assignee: Chevron Research Company, San Francisco, Calif.

[22] Filed: May 15, 1974

[21] Appl. No.: 470,234

Related U.S. Application Data

[62] Division of Ser. No. 280,608, Aug. 14, 1972, Pat. No. 3,845,091.

[52] U.S. Cl. .......................... 260/479 C; 260/482 C
[51] Int. Cl.² ...................................... C07C 125/06
[58] Field of Search ..................... 260/479 C, 482 C

[56] References Cited

UNITED STATES PATENTS 3,079,302 2/1963 Bergel et al. ..................... 260/482
3,167,472 1/1965 Czyzewski et al. ................ 260/479

*Primary Examiner*—James A. Patten
*Attorney, Agent, or Firm*—G. F. Magdeburger; D. A. Newell; Raymond Owyang

[57] ABSTRACT

This invention relates to novel N-alkyl-N-cyanoformyl carbamates and N-alkyl-N-cyanoformyl thiolcarbamates and their use as namatocides.

6 Claims, No Drawings

NEMATOCIDAL N-CYANOFORMYL CARBAMATES

This application is a division of U.S. Ser. No. 280,608, filed Aug. 14, 1972, now U.S. Pat. No. 3,845,091.

DESCRIPTION OF THE PRIOR ART

Netherlands patent application No. 6,500,321 (*Chem. Abs.* 64, 9633g[1966]) discloses certain N-cyanothioformyl carbamates as useful insecticides, fungicides, bactericides, herbicides, etc. Applicant's U.S. application Ser. No. 70,498, filed Sept. 8, 1970, now U.S. Pat. No. 3,705,188, common assignee, discloses O-naphthyl-N-cyanoformyl carbamates.

DESCRIPTION OF THE INVENTION

The N-cyanoformyl carbamates and N-cyanoformyl thiolcarbamates of the invention are represented by the formulas (I) and (II)

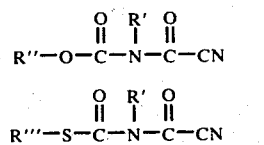

wherein R' is alkyl of 1 to 6 carbon atoms, R'' is alkyl of 1 to 10 carbon atoms (preferably of 1 to 6 carbon atoms), alkenyl of 2 to 10 carbon atoms (preferably of 3 to 6 carbon atoms), cycloalkyl of 3 to 10 carbon atoms (preferably of 5 to 8 carbon atoms), biphenyl, phenyl, aralkyl of 7 to 10 carbon atoms or phenyl substituted with from 1 to 3 groups selected from fluorine, chlorine, bromine and alkyl of 1 to 6 carbon atoms, and R''' is R''.

Suitable R' groups include methyl, ethyl, n-propyl, isopropyl, n-butyl, pentyl, hexyl, etc. The preferred R' group is methyl.

Suitable alkyl R'' and R''' include methyl, ethyl, n-propyl, n-butyl, isopentyl, hexyl, octyl, n-nonyl, n-decyl, etc. Suitable R'' and R''' alkenyl groups include vinyl, allyl, allyl, 2-butenyl, 3-hexyl, 5-heptenyl, 4-octenyl, 2-decenyl, etc. Suitable cycloalkyl R'' and R''' groups include cyclopropyl, cyclobutyl, cyclopentyl, 2-methylcyclopentyl, cyclopentylmethyl, cyclohexyl, cyclohexylmethyl, cycloheptyl, cyclooctyl, etc.

Suitable biphenyl R'' and R''' groups include o-, m- and p-biphenyl. Suitable aralkyl R'' and R''' groups include benzyl, 2-phenylethyl, 3-phenylpropyl, 3-tolylpropyl, etc. Suitable substituted-phenyl R'' and R''' groups include 2-methylphenyl, 3-methylphenyl, 2,4-dimethylphenyl, 3-isopropylpheyl, 3-sec-butylphenyl, 3-sec-amylphenyl, 2-fluorophenyl, 2,4-defluorophenyl, 3-chlorophenyl, 3,5-dichlorophenyl, 3-bromophenyl, 2,4,6-tribromophenyl, 2-chloro-4-methylphenyl, 2-fluoro-4-chlorophenyl, 3-fluoro-4-chlorophenyl, 2-fluoro-4-methylphenyl, 2-bromo-4-ethylphenyl, etc.

Representative N-cyanoformyl carbamates of formula (I) include O-methyl-N-methyl-N-cyanoformyl carbamate, O-ethyl-N-methyl-N-cyanoformyl carbamate, O-isobutyl-N-methyl-N-cyanoformyl carbamate, O-hexyl-N-methyl-N-cyanoformyl carbamate, O-decyl-N-ethyl-N-cyanoformyl carbamate, O-vinyl-N-methyl-N-cyanoformyl carbamate, O-allyl-N-methyl-N-cyanoformyl carbamate, 0-2-hexenyl-N-methyl-N-cyanoformyl carbamate, O-cyclopentyl-N-methyl-N-cyanoformyl carbamate, O-cyclohexyl-N-methyl-N-cyanoformyl carbamate, O-m-biphenyl-N-isopropyl-N-cyanoformyl carbamate, O-phenyl-N-methyl-N-cyanoformyl carbamate, O-phenyl-N-ethyl-N-cyanoformyl carbamate, O-phenyl-N-hexyl-N-cyanoformyl carbamate, O-benzyl-N-methyl-N-cyanoformyl carbamate, 0-4-fluorophenyl-N-methyl-N-cyanoformyl carbamate, 0-2-chlorophenyl-N-butyl-N-cyanoformyl carbamate, 0-3,4-dichlorophenyl-N-methyl-N-cyanoformyl carbamate, 0-2-methylphenyl-N-methyl-N-cyanoformyl carbamate, 0-3-sec-butylphenyl-N-methyl-N-cyanoformyl carbamate, 0-3,5-diethylphenyl-N-methyl-N-cyanoformyl carbamate, 0-2-chloro-4-methylphenyl-N-methyl-N-cyanoformyl carbamate, 0-2-fluoro-4-methylphenyl-N-methyl-N-cyanoformyl carbamate, and 0-2-ethyl-3-bromophenyl-N-methyl-N-cyanoformyl carbamate.

Representative N-cyanoformyl thiolcarbamates of formula (II) include S-methyl-N-methyl-N-cyanoformyl thiolcarbamate, S-ethyl-N-ethyl-N-cyanoformyl thiolcarbamate, S-isopropyl-N-isopropyl-N-cyanoformyl thiolcarbamate, S-n-pentyl-N-n-pentyl-N-cyanoformyl thiolcarbamate, S-n-nonyl-N-methyl-N-cyanoformy thiolcarbamate, S-vinyl-N-methyl-N-cyanoformyl thiolcarbamate, S-allyl-N-methyl-N-cyanoformyl thiolcarbamate, S-2-butenyl-N-methyl-N-cyanoformyl thiolcarbamate, S-cyclopropyl-N-methyl-N-cyanoformyl thiolcarbamate, S-cyclohexyl-N-methyl-N-cyanoformyl thiolcarbamate; S-o-biphenyl-N-methyl-N-cyanoformyl thiolcarbamate, S-phenyl-N-methyl-N-cyanoformyl thiolcarbamate, S-benzyl-N-methyl-N-cyanoformyl thiolcarbamate, S-2-fluorophenyl-N-methyl-N-cyanoformyl thiolcarbamate, S-3-bromophenyl-N-methyl-N-cyanoformyl thiolcarbamate, S-2,4-dichlorophenyl-N-methyl-N-cyanoformyl thiolcarbamate, S-4-methylphenyl-N-methyl-N-cyanoformyl thiolcarbamate, S-3-sec-pentylphenyl-N-methyl-N-cyanoformyl thiolcarbamate, S-4-t-butylphenyl-N-methyl-N-cyanoformyl thiolcarbamate, S-3,5-dimethylphenyl-N-methyl-N-cyanoformyl thiolcarbamate, S-2,4-dimethylphenyl-N-methyl-N-cyanoformyl thiolcarbamate, S-2,4-dipropyl-phenyl-N-methyl-N-cyanoformyl thiolcarbamate and S-2-fluoro-4-methylphenyl-N-methyl-N-cyanoformyl thiolcarbamate.

Other compounds of the invention include compounds of formulas (I) and (II) wherein R'' and R''' is a 2,3-dihydro-2,2-dialkyl-7-benzofuranyl group. Representative of such compounds include 0-(2,3-dihydro-2,2-dimethyl-7-benzofuranyl)-N-methyl-N-(cyanoformyl)carbamate and S-(2,3-dihydro-2,2-dimethyl-7-benzofuranyl)-N-methyl-N-(cyanoformyl)thiolcarbamate.

The compounds of formula (I) and (II) are prepared by the reaction of a N-alkyl cyanoformamide and a thiochloroformate or chloroformate in the presence of an acid acceptor as depicted in equation (1):

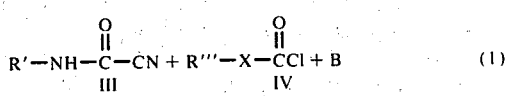

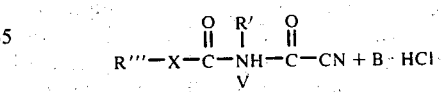

wherein R' and R" are as defined above, X is oxygen or sulfur and B is an acid acceptor.

The reaction is conducted by conventional procedures. Generally, the reactants are contacted in substantially equimolar amounts. Suitable acid acceptors include organic base such as pyridine, triethylamine or dimethylaniline. The reaction is suitably conducted in inert solvents, e.g., hydrocarbon solvents such as benzene, at temperatures from 0° to 50°C. The product is then isolated by conventional procedures such as extraction, distillation, chromatography, etc.

Alternatively, the carbamates of formula (I) and (II) are prepared by the reaction of an alcohol or a mercaptan and a N-methyl-N-chlorocarbonyl cyanoformamide in the presence of an acid acceptor as depicted in equation (2):

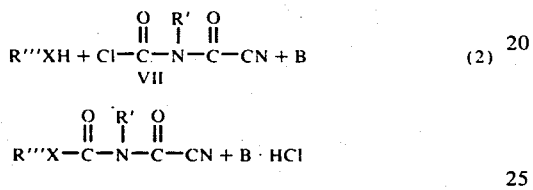

wherein R', R''', X and B are as defined above. This reaction is conducted by essentially the same procedures employed for reaction depicted in equation (2). The N-methyl-N-chlorocarbonyl cyanoformamide (VII) is prepared by the reaction of the N-alkyl cyanoformamide (III) and phoseine in the presence of an acid acceptor by conventional procedures.

EXAMPLE 1

Preparation of S-phenyl-N-methyl-N-cyanoformyl thiolcarbamate

A 10.1 g. (0.1 mol) sample of triethylamine was added dropwise to a solution of 17.3 g. (0.1 mol) phenyl chlorothioformate and 8.4 g. (0.1 mol) N-methyl cyanoformamide in benzene at a temperature of about 25°C. After the addition was completed, the reaction mixture was stirred for 2 hours at 25°C and filtered. The filtrate was evaporated under reduced pressure to give a brown residue. The residue was washed with water and ethanol to give a white solid product, m.p. 155°–159°C. Elemental analysis on the product is tabulated in Table I.

EXAMPLE 2

Preparation of S-4-chlorophenyl-N-methyl-N-cyanoformyl carbamate

A 7.3 g. (0.06 mol) sample of N,N-dimethylaniline was added dropwise to a solution of 8.5 g. (0.055 mol) N-methyl-N-chlorocarbonyl cyanoformamide and 7.9 g. (0.55 mol) 4-chlorophenyl mercaptan in 75 ml. benzene at about 0°–10°C. After the addition was completed, the reaction mixture was stirred for 1 hour at about 25°C. The reaction mixture was then washed successively with water, 10% hydrochloric acid solution, and water, dried over magnesium sulfate and evaporated under reduced pressure to give a tan solid product. The product was then washed with ethanol and dried. The melting point and elemental analysis of the product is tabulated in Table I.

EXAMPLE 3

Preparation of O-n-butyl-N-methyl-N-cyanoformyl carbamate

A 10.1 g. (0.1 mol) sample of triethylamine was added dropwise to a solution of 13.7 g. (0.1 mol) n-butyl chloroformate and 8.4 g. (0.1 mol) N-methyl cyanoformamide in benzene at a temperature of about 25°C. After the addition was completed, the reaction mixture was stirred for 2 hours at 25°C and filtered. The filtrate was evaporated under reduced pressure to give the product as a brown oil. Elemental analysis on the product is tabulated in Table I.

The compounds tabulated in Table I were prepared by the procedures described in Examples 1–3.

TABLE I

| COMPOUND | MELTING POINT, °C | SULFUR Calc. | SULFUR Found | NITROGEN Calc. | NITROGEN Found |
|---|---|---|---|---|---|
| S-ethyl-N-methyl-N-cyanoformyl thiolcarbamate | Oil | 18.6 | 17.1 | — | — |
| S-phenyl-N-methyl-N-cyanoformyl thiolcarbamate | 155–159 | 14.5 | 14.2 | — | — |
| S-4-chlorophenyl-N-methyl-N-cyanoformyl thiolcarbamate | 129–132 | 12.6 | 12.5 | 13.9 (Cl) | 14.9 (Cl) |
| S-4-methylphenyl-N-methyl-N-cyanoformyl thiolcarbamate | 126–128 | 13.7 | 13.4 | 12.0 | 12.2 |
| S-4-t-butylphenyl-N-methyl-N-cyanoformyl thiolcarbamate | Oil | 11.6 | 12.0 | — | — |
| O-2,4-dichloro-6-methylphenyl-N-methyl-N-cyanoformyl carbamate | 115–117 | 24.7 (Cl) | 23.7 | — | — |
| O-4-chloro-3-methylphenyl-N-methyl-N-cyanoformyl carbamate | 96–100 | 14.1 (Cl) | 14.5 | — | — |
| O-n-butyl-N-methyl-N-cyanoformyl carbamate | Oil | 52.2 (C) 6.5 (H) | 52.9 (C) 7.1 (H) | 15.2 | 16.1 |
| O-phenyl-N-methyl-N-cyanoformyl carbamate | 93–98 | 8.9 (C) 3.9 (H) | 61.8 (C) 4.0 (H) | 13.7 | 13.1 |
| O-ethyl-N-methyl-N-cyanoformyl-carbamate | Oil | 46.2 (C) 5.2 (H) | 46.5 (C) 5.7 (H) | 18.0 | 20.1 |
| O-3-sec-amylphenyl-N-methyl-N-cyanoformyl-carbamate | Oil | — | — | 10.2 | 9.6 |

UTILITY

The compounds of the invention have exhibited biological activity against a variety of organisms, particularly nematodes, when applied in biocidally effective amounts to such organisms.

The compounds of the invention are particularly effective killers of soil-dwelling nematodes—that is, the unsegmented roundworms of the class Nematoda, also known as eelworms, which customarily inhabit soil and feed upon the roots of plants growing therein. Included are the cyst forming nematodes of the genus Heterodera (e.g. the golden nematode [*Heterodera rostochiensis*]), the stubby root nematodes of the genus Trichodorus, the bulb and stem nematodes of the genus Ditylenchus, the root knot nematodes of the genus Meloidogyne, the root-lesion nematodes of the genus Pratylenchus, the citrus nematodes of the genus Tylenchulus, the sting nematodes of the genus Balonolaimus, and the plant-parasitic nematodes of such genera as Nacobus, Radopholus, and the like.

The compounds of the invention are employed for the destruction of nematodes in soil by disseminating the compounds in the nematode-infested soil, in nematocidally effective concentrations. The nematocidally effective concentrations in the soil lie within the range of from about 1 to about 500 parts per million, on a weight basis based on the weight of the air-dry soil, with the usual dosage ranging from about 4 to about 20 parts per million, on the same basis. As a practical matter, the effective dosage generally amounts to from about 1 to about 100 pounds of the nematicide per acre of land, depending upon the depth of soil to be treated, which may be up to 6, or 8, or even 12 inches, depending upon the particular species of plants and nematodes involved. Generally, dosages of from about 2 to about 40 pounds of the nematicide per acre of land are preferred.

Some of the compounds of the invention are solids at ordinary room temperature. These may be applied to the soil neat—as by grinding the solids, then admixing the resulting dust or powder with the soil to be treated. Alternatively, the compounds may be dissolved in a suitable liquid diluent and the solution applied to and mixed with the soil, or the compounds may be formulated with a suitable solid carrier and applied as a dust, powder or as granules to the soil and admixed therewith. By the use of suitable emulsifying and dispersing agents, the compounds can be emulsified and dispersed in water and the emulsion applied to the soil to be treated to provide effective control of the nematodes therein. Any of the usual emulsifying and dispersing agents commonly employed in forming aqueous emulsions and suspensions of water-insoluble materials can be used for this purpose. Generally only a small concentration of the emulsifying agents is required, as little as 0.05 percent of the weight of the final formulation being effective in many cases, while seldom will more than about 10% of the weight of the final formulation be required. Usually the concentration of the emulsifying or dispersing agent will be from about 0.5 to about 5 percent of the weight of the formulation. Alternatively, or in addition, in some cases it may be to advantage to dissolve the compounds to be used in a solvent which can readily be dispersed in water to produce a heterogeneous dispersion of the nematicide in the water.

Where the compounds are to be applied as a solution, suitable solvents include alcohols, ketones and hydrocarbons, such as, for example, isopropyl alcohol, benzene, acetone, methyl ethyl ketone, secondary butyl alcohol, kerosine, chlorinated hydrocarbons, various non-phytotoxic hydrocarbon fractions which are ordinarily used in disseminating agricultural chemicals, including spray oils, horticultural oils, and the like.

The suitable solid carriers ordinarily are those which are essentially inert in the soil and which are not hydroscopic—for if they are hydroscopic the final formulation will not remain dry and free-flowing. In some cases, however, it may be desirable to employ as carrier a solid which is not inert—as, for example, a solid fertilizer such as a commercial mixed solid fertilizer, rock phosphate, urea or the like. Suitable inert carriers are those well known to the art including the clays such as the kaolinites, the bentonites and the attapulgites; other minerals in natural state such as talk, pyrophyllite, quartz, diatomaceous earth, fuller's earth, chalk, rock phosphate and sulphur; and chemically modified minerals, such as acid washed bentonites, precipitated calcium phosphates, precipitated calcium carbonate, and colloidal silica. These diluents may represent a substantial portion; for example, 50 to 98 percent by weight of the entire formulation.

These solid formulations can be prepared by grinding or airmilling the carrier and nematicide together. Alternatively, the solid formulations can be formed by dissolving the nematicide in a suitable solvent, such as a volatile solvent, impregnating and/or coating the particles with the solution and if necessary, removing the solvent. The formulation also can be effected by melting the nematicide and mixing the molten nematicide with the carrier. Granular formulations can be prepared by impregnating and/or coating granules of the carrier with the nematicide or by forming granules of mixtures of the nematicide and carrier.

From the standpoint of mechanics, the nematicide, neat or as a formulation, is applied to the soil in any manner which enables an intimate admixture with the soil to be obtained. Thus the nematicide, which includes formulations thereof, can be applied to the surface of the soil, or it can be applied below the surface of the soil, and then admixed with the soil. If in the form of a liquid formulation, the nematicide can be drenched onto the surface of the soil or injected into the soil. Other conventional means, well known in the art, can be used to effect intimate admixture of the nematicide with the soil to be treated.

The formulations of the nematicides may also contain other materials, such as insecticides, fungicides, nematicides or different action and/or different physical characteristics, hormones, and/or fertilizers, to form multipurpose compositions.

EXAMPLE 4

Nematode Control

The compounds of the invention were tested for nematocidal activity by the following method: a 0.38 ml. portion of a 3% acetone solution of the test compound was diluted with 1 ml. acetone. The resulting slution was homogenously mixed with 20 cc. of vermiculite. The treated vermiculite was then mixed homogenously with 750 g. of soil, dry weight basis, which was severely infested with free-living nematodes (mixed culture of *Meloidogyne javanica* and *Meloidogyne incognita*). This mixing gave a concentration of approximately 15 parts of the test compound per million parts of soil. This treated soil was stored for 4 days at 65°–75°F. It was then divided equally into 3 parts, each of which was put into a separate pot and kept for another 3 days. A 3-week old tomato (v. Bonny Best) seedling was then transplanted into each pot and incubated for 13 days under greenhouse conditions. After this period they were removed and the soil was washed from their roots. The nematocidal effectiveness of the test compound was determined by observing each plant for signs of nematode invasion (number of galls formed, stunting, etc.).

The results of these tests, reported as the average of the 3 replicates on a 0 to 100 basis — indicating no effectiveness; 100 indicating complete effectiveness — are reported in Table II.

TABLE II

| COMPOUND | NEMATOCIDAL CONTROL, % |
|---|---|
| S-ethyl-N-methyl-N-cyanoformyl thiolcarbamate | 69 |
| S-phenyl-N-methyl-N-cyanoformyl thiolcarbamate | 90 |
| S-4-chlorophenyl-N-methyl-N-cyanoformyl thiolcarbamate | 100 |
| S-4-methylphenyl-N-methyl-N-cyanoformyl thiolcarbamate | 99 |
| O-n-butyl-N-methyl-N-cyanoformyl carbamate | 83 |
| O-phenyl-N-methyl-N-cyanoformyl carbamate | 83 |
| O-ethyl-N-methyl-N-cyanoformyl carbamate | 83 |
| O-phenyl-N-methyl-N-cyanothioformyl carbamate | 0 |

EXAMPLE 5

Fungi Control 0-2,4-dichloro-6-methylphenyl-N-methyl-N-cyanoformyl carbamate, 0-4-chloro-3-methylphenyl-N-methyl-N-cyanoformyl carbamate, and 0-p-biphenyl-N-cyanoformyl carbamate were tested for the control of *Uromyces phaseoli typica* by the following procedure.

Pinto bean seedlings were sprayed with solutions of the test compound (250 ppm) mixed with acetone, water and a small amount of a non-ionic emulsifier. The sprayed seedlings were then inoculated with the fungus organism and incubated in a chamber maintained at 66°–88°F and 100% relative humidity for about 20 hours. Following the incubation, the seedlings were allowed to dry and then transferred to a greenhouse maintained at 66°–68°F and 60–80% relative humidity for about 14 days.

The percent fungi control provided by a given test compound was based on the percent fungi reduction relative to untreated check seedlings. The three compounds tested each gave at least 62% fungi control.

I claim:

1. A compound of formula

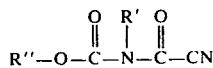

wherein R' is alkyl of 1 to 6 carbon atoms and R'' is alkyl of 1 to 10 carbon atoms, alkenyl of 2 to 10 carbon atoms, cycloalkyl of 3 to 10 carbon atoms, biphenyl, phenyl, hydrocarbon aralkyl of 7 to 10 carbon atoms, or phenyl substituted with from 1 to 3 groups selected from fluorine, chlorine, bromine and alkyl of 1 to 6 carbon atoms.

2. The compound of claim 1 wherein R'' is alkyl of 1 to 6 carbon atoms.

3. The compound of claim 2 wherein R'' is n-butyl and R' is methyl.

4. The compound of claim 1 wherein R'' is biphenyl, phenyl or phenyl substituted with 1 to 3 groups selected from fluorine, chlorine, bromine or alkyl of 1 to 6 carbon atoms.

5. The compound of claim 1 wherein R'' is phenyl and R' is methyl.

6. The compound of claim 1 wherein R'' is biphenyl and R' is methyl.

* * * * *